United States Patent
Peng et al.

(10) Patent No.: US 11,116,735 B2
(45) Date of Patent: Sep. 14, 2021

(54) USE OF SUBSTITUTED BENZYLIDENEGUANIDINE DERIVATIVES AS SYNERGISTS FOR POLYMYXIN ANTIBIOTICS

(71) Applicant: GUANGZHOU INSIGHTER BIOTECHNOLOGY CO., LTD., Guangzhou (CN)

(72) Inventors: Xianfeng Peng, Guangzhou (CN); Zonghua Qin, Guangzhou (CN)

(73) Assignee: GUANGZHOU INSIGHTER BIOTECHNOLOGY CO., LTD., Guangzhou (CN)

( * ) Notice: Subject to any disclaimer, the term of this patent is extended or adjusted under 35 U.S.C. 154(b) by 436 days.

(21) Appl. No.: 16/474,071

(22) PCT Filed: Mar. 30, 2016

(86) PCT No.: PCT/CN2016/077916
§ 371 (c)(1),
(2) Date: Jun. 27, 2019

(87) PCT Pub. No.: WO2017/005018
PCT Pub. Date: Jan. 12, 2017

(65) Prior Publication Data
US 2020/0016099 A1 Jan. 16, 2020

(30) Foreign Application Priority Data
Jul. 9, 2015 (CN) .......................... 201510401029.5

(51) Int. Cl.
| A61K 31/155 | (2006.01) |
| A23K 20/195 | (2016.01) |
| A23K 50/30 | (2016.01) |
| A23K 50/60 | (2016.01) |
| A23K 20/111 | (2016.01) |
| A61P 31/04 | (2006.01) |
| A61K 9/00 | (2006.01) |

(52) U.S. Cl.
CPC .......... *A61K 31/155* (2013.01); *A23K 20/111* (2016.05); *A23K 20/195* (2016.05); *A23K 50/30* (2016.05); *A23K 50/60* (2016.05); *A61K 9/0056* (2013.01); *A61P 31/04* (2018.01)

(58) Field of Classification Search
CPC ........ A61P 31/04; A61K 38/12; A61K 31/155
See application file for complete search history.

(56) References Cited

U.S. PATENT DOCUMENTS

| 3,769,432 A | 10/1973 | Tomcufcik |
| 3,901,944 A | 8/1975 | Tomcufcik |
| 3,941,825 A | 3/1976 | Tomcufcik |
| 3,992,446 A | 11/1976 | Tomcufcik |
| 4,310,541 A | 1/1982 | Wang et al. |
| 4,575,560 A | 3/1986 | Addor et al. |
| 9,539,223 B2 * | 1/2017 | Page .................... A61K 9/0014 |
| 9,663,458 B2 * | 5/2017 | Peng .................... A23K 50/75 |
| 10,253,002 B2 * | 4/2019 | Page ........................ A61P 7/00 |
| 2017/0073373 A1 * | 3/2017 | Brown .................. A61K 38/00 |

FOREIGN PATENT DOCUMENTS

| CN | 1093081 A | 10/1994 | |
| CN | 103284007 A | 9/2013 | |
| CN | 103880712 A | 6/2014 | |
| CN | 104082534 A | 10/2014 | |
| CN | 104082621 A | 10/2014 | |
| CN | 104744312 A | 7/2015 | |
| CN | 104744313 A | 7/2015 | |
| CN | 105030744 A | 11/2015 | |
| WO | 0040549 A1 | 7/2000 | |
| WO | 2014176634 A1 | 11/2014 | |
| WO | 2014176636 A1 | 11/2014 | |
| WO | WO-2014176636 A1 * | 11/2014 | ............... A61P 9/00 |

OTHER PUBLICATIONS

Storm et al., "Polymyxin and Related Peptide Antibiotics", 1977, Ann. Rev. Biochem., 46, pp. 723-763 (Year: 1977).*
Evans et al., "Polymyxin B Sulfate and Colistin: Old Antibiotics for Emerging Multiresistant Gram-Negative Bacteria", 1999, The Annals of Pharmacotherapy, vol. 33, pp. 960-967. (Year: 1999).*
National Center for Biotechnology Information. "PubChem Compound Summary for CID 5311054, Colistin" PubChem, https://pubchem.ncbi.nlm.nih.gov/compound/Colistin. Created Dec. 16, 2005. Accessed Mar. 18, 2021. (Year: 2005).*
Turner et al., "Administration of Substances to Laboratory Animals: Routes of Administration and Factors to Consider", 2011, Journal of the American Association for Laboratory Animal Science, vol. 50, No. 5, pp. 600-613. (Year: 2011).*
Organic Chemistry, Third Edition, Hu Honh-Wen, p. 296.

* cited by examiner

*Primary Examiner* — My-Chau T. Tran

(74) *Attorney, Agent, or Firm* — Bayramoglu Law Offices LLC

(57) ABSTRACT

A use of a substituted benzoguanidine derivative as a polymyxin antibiotic synergist, particularly as a synergist and a drug resistance reversal agent of the polymyxin antibiotic for inhibiting a sensitive strain, or a composition comprising the same in combination with a polymyxin antibiotic for preparing a compound pharmaceutical preparation for human or animal use in the treatment of a disease caused by a gram-negative bacterial infection or the preparation a growth-promoting feed additive and for the raising of livestock animals.

8 Claims, No Drawings

USE OF SUBSTITUTED BENZYLIDENEGUANIDINE DERIVATIVES AS SYNERGISTS FOR POLYMYXIN ANTIBIOTICS

CROSS REFERENCE TO THE RELATED APPLICATIONS

This application is the national phase entry of International Application No. PCT/CN2016/077916, filed on Mar. 30, 2016, which is based upon and claims priority to Chinese Patent Application No. 201510401029.5, filed on Jul. 9, 2015, the entire contents of which are incorporated herein by reference.

TECHNICAL FIELD

The present invention relates to the biomedical field, and particularly relates to the use of substituted benzylideneguanidine derivatives as synergists for polymyxin antibiotics.

BACKGROUND

Studies on the chemical synthesis and biological application of diaminoguanidines, especially substituted benzylideneguanidine derivatives, started very early, and their main findings include the followings. The substituted benzylideneguanidine derivatives disclosed in U.S. Pat. No. 4,310,541A are used in treating trichomoniasis and antiparasites for humans. The substituted benzylideneguanidine derivatives provided in U.S. Pat. No. 4,575,560A are used in agricultural production, exhibit antifeeding activity and are effective in controlling lepidopterous insects, and thus are useful for protecting agronomic crops. The substituted benzylideneguanidine derivatives provided in US399244 are used as antiprotozoal agents and especially anticoccidial agents. The substituted benzylideneguanidine derivatives provided in WO2014176636A1 are used in treating bacterial infections for animals such as mammals, fish, avian, humans, canines, cats, pigs and horse, against bacteria such as Gram-positive bacteria, Gram-negative bacteria and cell wall free bacteria. As in China, CN104082534A and CN104082621A relate to the use of robenidine in livestock husbandry as a growth promoter in feed for pigs or ducks, and CN103880712A discloses a chemical preparation method of diaminoguanidines derivatives and the use thereof in preparing a growth promoter in animal feed.

Polymyxins are a group of antimicrobial polypeptides found in the culture broth of *Bacillus polymyxa*, consisting of five different compounds named as polymyxins A, B, C, D, and E, which are similar in structure, exhibit similar broad antibacterial spectra, and especially have a strong effect against Gram-negative bacteria.

Polymyxin E is commonly used clinically in the form of polymyxin E sulfate and polymyxin E sodium methanesulfonate. Polymyxin E sulfate, also known as colistin sulfate, colistin and Kang-Di-Su (a Chinese name), functions mainly by binding to the free phosphate ester salts of lipoproteins in the cell membrane of bacteria and thereby causing a strong interaction, which reduces the surface tension of the cytoplasmic membrane and increases its permeability leading to leakage of intracellular contents (especially purines and pyrimidines) from the cytoplasm and bacterial death. Polymyxin E is an antibiotic that acts on stationary phase bacteria, exhibits a relatively narrow antibacterial spectrum and especially a strong antibacterial activity on Gram-negative bacteria. Susceptible bacteria include *Pseudomonas aeruginosa*, *Escherichia coli*, Enterobacteriaceae, *Klebsiella*, *Salmonella*, *Shigella*, *Pasteurella*, and *Vibrio*, while *Proteus*, *Brucella*, *Serratia* and all the Gram-positive bacteria are resistant to polymyxin E. Polymyxin E is heat-resistant, hardly adsorbed from the digest tract, excreted rapidly, and low toxic. It was once one of the antibiotics for Gram-negative bacteria in humans and animals and one of the most widely used and safest growth-promoting antibiotics for livestock and poultry, and used in the treatment of intestinal diseases caused by Gram-negative bacteria and as a feed additive.

At present, the application of polymyxin antibiotics in production and life is greatly affected by the problem of drug resistance in bacteria. In practice, a variety of drugs have been used in combination with polymyxin antibiotics in order to increase the efficacy, while it has been proven via experiments that the therapeutic effect, of each combination of polymyxin antibiotics and these compatible drugs, is merely a sum of the inhibitory effect of each drug on different bacteria, without providing any synergistic effect on the efficacy of polymyxin antibiotics. Moreover, these compatible drugs are antibacterial agents, bactericides, or chemical agents with certain toxicity, such that a long-term application may lead to the emergence of new multidrug-resistant strains or cause serious pollution to the environment; for some of these drugs, their uses as feed additives have been banned by the European Union, Thus, to discover novel non-bactericidal and non-antibacterial synergistic agents or resistance-reversal agents for polymyxin antibiotics, which are low-toxic or non-toxic, will be the most effective means to overcome the difficulties caused by polymyxin antibiotics in practical use.

SUMMARY

The first object of the present invention is to provide the use of a substituted benzylideneguanidine derivative, a stereoisomer thereof, a geometric isomer thereof, a tautomer thereof, a hydrate thereof, a solvate thereof, a metabolite thereof, a pharmaceutically acceptable salt thereof, a prodrug thereof, or a composite comprising the same, as a synergist for polymyxin antibiotics, the substituted benzylideneguanidine derivative having a structure according to formula (I):

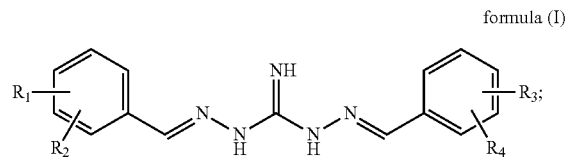

formula (I)

wherein, $R_1$, $R_2$, $R_3$ and $R_4$ are H, CN, $NO_2$, $S(=O)_2CH_3$, $C(=O)O-C_{1-8}$ linear or branched alkyl, halogen, $C_{1-8}$ linear or branched alkyl, $C_{1-8}$ linear or branched alkyl halide, $O-C_{1-14}$ linear or branched alkyl, $O-C_{3-8}$ cycloalkyl, $O-CH_2$-Ph, O-Ph, $S-C_{1-14}$ linear or branched alkyl, or $S-C_{1-14}$ linear or branched alkyl halide;

the halogen is F, Cl, Br or I;

the alkyl halide is an F, Cl, Br, or I substituted alkyl;

the phenyl of the $O-CH_2$-Ph or O-Ph is a unsubstituted phenyl or a phenyl substituted with one, two, three, or four substituents, the substituents being selected from F, Cl, Br, I, $C_{3-8}$ cycloalkyl, and $C_{1-8}$ linear or branched alkyl.

Preferably, the substituted benzylideneguanidine derivative has a structure according to formula (II):

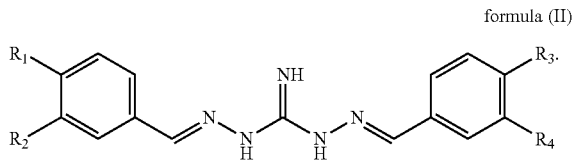

formula (II)

Further preferably, the $R_1$ and the $R_3$ are identical, and the $R_2$ and the $R_4$ are identical.

In some embodiments, the $R_1$ and the $R_3$ are both $O-C_{1-14}$ linear or branched alkyl, and the $R_2$ and the $R_4$ are both H. Preferably, the substituted benzylideneguanidine derivative has a structure according to formula (III):

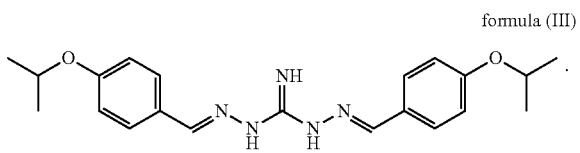 [SMILES: CC(C)Oc1ccc(/C=N/NC(=N)N/N=C/c2ccc(OC(C)C)cc2)cc1]

formula (III)

In some other embodiments, the compound is provided that $R_1$ and the $R_3$ are both halogen and the $R_2$ and the $R_4$ are both H. Preferably, the substituted benzylideneguanidine derivative has a structure according to formula (IV):

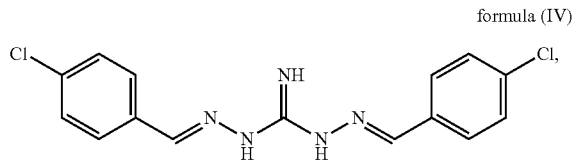 [SMILES: N=C(N/N=C/c1ccc(Cl)cc1)N/N=C/c1ccc(Cl)cc1]

formula (IV)

In some other embodiments, the pharmaceutically acceptable salt of the substituted benzylideneguanidine derivative is a hydrochloride, a phosphate, a sulfate, an acetate, a lactate, a methanesulfonate, a 2-hydroxyethylsulfonate, a succinate, a benzoate, a tartrate, a citrate, a lysine salt, a fumarate or a maleate of the substituted benzylideneguanidine derivative.

The prior art WO2014176636A1 suggests the use of diaminoguanidine derivatives in treating bacterial infections for animals such as mammals, fish, avian, humans, canines, cats, pigs and horse, against bacteria such as Gram-positive bacteria, Gram-negative bacteria and cell wall free bacteria. In the light of the protocols and ideas provided in WO2014176636A1, the inventors conducted in-depth research on the biological activity of diaminoguanidine derivatives but unexpectedly found that, the diaminoguanidine derivatives had an inhibitory effect on anaerobic Gram-positive bacteria while no inhibitory activity against Gram-negative bacteria was observed in the bacteriostatic test. Based on the above accidental findings, in some embodiments, the inventors further measured the minimum inhibitory concentrations of the substituted benzylideneguanidine derivatives against Gram-negative bacteria, and the test results showed that the substituted benzylideneguanidine derivatives had no inhibitory activity against Gram-negative bacteria. In some other embodiments, in vitro minimum inhibitory concentrations of polymyxin antibiotics against their corresponding susceptible bacteria were measured where the cultures respectively comprised substituted benzylideneguanidine derivatives of various structures in the same concentration, showing that the substituted benzylideneguanidine derivatives significantly increase the inhibitory effect. In some other embodiments, in vitro minimum inhibitory concentrations of polymyxin antibiotics against their corresponding susceptible bacteria were measured where the medium respectively comprised substituted benzylideneguanidine derivatives of various structures in the same concentration, and a preferred susceptible bacterium for test is *Escherichia coli* which is sensitive to polymyxin antibiotics. In some other embodiments, in vitro minimum inhibitory concentrations of polymyxin antibiotics against their corresponding resistant bacteria were measured where the medium respectively comprised substituted benzylideneguanidine derivatives of various structures in the same concentration, showing that the substituted benzylideneguanidine derivatives significantly increase the inhibitory effect by exhibiting a drug-resistance reversing effect. In some other embodiments, the substituted benzylideneguanidine derivative of the same structure in various concentrations exhibited a dosage-dependent potentiation in the inhibitory effect against the polymyxin antibiotic-resistant bacteria.

In the present invention, the polymyxin antibiotic involved in the research is any one of polymyxin A, polymyxin B, polymyxin C, polymyxin D, polymyxin E, pharmaceutically acceptable salts thereof, or prodrugs thereof.

In some embodiments, the polymyxin antibiotic involved is preferably colistin sulfate.

In some embodiments, the polymyxin antibiotic involved is preferably polymyxin E sodium methanesulfonate.

In the synergistic inhibition experiments of the substituted benzylideneguanidine derivatives towards polymyxin antibiotics, significant synergistic effects were observed in the potentiation and resistance reversal caused by the substituted benzylideneguanidine derivatives and the dosage-response relationship.

In some other embodiments, various substituted benzylideneguanidine derivatives were used in combination with polymyxin antibiotics in the feeding of weanling piglets, broilers, and meat ducks. The diarrhea rate, weight gain and feed efficiency were studied on piglets, broilers and meat ducks fed with the compounds, and the results showed a significant synergistic effect in growth promotion.

Thus, the substituted benzylideneguanidine derivative, the stereoisomer thereof, the geometric isomer thereof, the tautomer thereof, the hydrate thereof, the solvate thereof, the metabolite thereof, the pharmaceutically acceptable salt thereof, the prodrug thereof, or the composite comprising the same, as described in the present invention, is used as a synergistic agent or resistance-reversal agent for polymyxin antibiotics.

The substituted benzylideneguanidine derivative, the stereoisomer thereof, the geometric isomer thereof, the tautomer thereof, the hydrate thereof, the solvate thereof, the metabolite thereof, the pharmaceutically acceptable salt thereof, the prodrug thereof, or the composite comprising the same, as described in the present invention, is used as a synergist for polymyxin antibiotics in preparing a drug against polymyxin antibiotic-susceptible bacteria or polymyxin antibiotic-resistant susceptible bacteria.

The susceptible bacteria can be *Escherichia coli, Pseudomonas aeruginosa, Salmonella, Shigella,* or *Klebsiella.*

The substituted benzylideneguanidine derivative, the stereoisomer thereof, the geometric isomer thereof, the tautomer thereof, the hydrate thereof, the solvate thereof, the metabolite thereof, the pharmaceutically acceptable salt thereof, the prodrug thereof, or the composite comprising the same, as described in the present invention, is used in combination with a polymyxin antibiotic, as an animal growth promoter which is a feed additive in animal feed. Further preferably, a concentration of the substituted benzylideneguanidine derivative, the stereoisomer thereof, the geometric isomer thereof, the tautomer thereof, the hydrate thereof, the solvate thereof, the metabolite thereof, the pharmaceutically acceptable salt thereof, the prodrug thereof, or the composite comprising the same, in the animal feed, is 1 to 300 ppm, and further preferably 20 to 90 ppm.

The substituted benzylideneguanidine derivative, the stereoisomer thereof, the geometric isomer thereof, the tautomer thereof, the hydrate thereof, the solvate thereof, the metabolite thereof, the pharmaceutically acceptable salt thereof, the prodrug thereof, or the composite comprising the same, as described in the present invention, is used in combination with a polymyxin antibiotic, in preparing a pharmaceutical composition for humans. The pharmaceutical composition comprises the substituted benzylideneguanidine derivative, one of the polymyxin antibiotics, and other excipients, and can be in the form of a pulvis, granule, tablet, capsule, unguent, eye ointment, gel, aerosol, film, oral solution, eye drop, injection, suppository, etc. The pharmaceutical composition can be used in treating deceases caused by Gram-negative bacteria infection, such as gastrointestinal infection, sepsis, urinary tract infection, dysentery, whooping cough, respiratory tract infection, biliary tract infection, and burn or traumatic wound infection caused by bacteria in human.

The substituted benzylideneguanidine derivative, the stereoisomer thereof, the geometric isomer thereof, the tautomer thereof, the hydrate thereof, the solvate thereof, the metabolite thereof, the pharmaceutically acceptable salt thereof, the prodrug thereof, or the composite comprising the same, as described in the present invention, is used in combination with a polymyxin antibiotic, in preparing a pharmaceutical composition for animals. The pharmaceutical composition for animals comprises the substituted benzylideneguanidine derivative, one of the polymyxin antibiotics, and other excipients, and can be in the form of a premix, oral solution, soluble powder, tablet, granule, pulvis, injection, etc. These pharmaceutical compositions for animals can be used as animal therapeutic drugs or feed additives for productive use, and applicable to animals including pigs, chicken, ducks, geese, pigeons, rabbits, mice, canines, cats, cattle, sheep, horses, donkeys, other furry animals, etc.

It is discovered for the first time by the inventors that substituted benzylideneguanidine derivatives can be used as synergists for polymyxin antibiotics, and especially as synergistic agents for polymyxin antibiotics in inhibiting susceptible bacteria and resistance-reversal agents for polymyxin antibiotics. The present invention also provides the use of the substituted benzylideneguanidine derivatives or the composite comprising the same in combination with the polymyxin antibiotics in preparing pharmaceutical compositions for humans or animals which are used for treating deceases caused by Gram-negative bacteria infection. The present invention further provides the use of the substituted benzylideneguanidine derivatives or the composite comprising the same in combination with the polymyxin antibiotics in preparing growth-promoting feed additives which are used in livestock farming.

DETAILED DESCRIPTION OF THE EMBODIMENTS

The following embodiments are intended to further illustrate the invention but not to limit the invention.

The substituted benzylideneguanidine derivatives used in the following embodiments are listed in Table 1.

TABLE 1

Substituted benzylideneguanidine derivatives in the embodiments

| Number | $R_1$ | $R_2$ | $R_3$ | $R_4$ |
|---|---|---|---|---|
| Compound 1 | $OCH_3$ | H | $OCH_3$ | H |
| Compound 2 | $OCH_2CH_3$ | H | $OCH_2CH_3$ | H |
| Compound 3 | O—(i-Pr) | H | O—(i-Pr) | H |
| Compound 4 | O—$(CH_2)_7CH_3$ | H | O—$(CH_2)_7CH_3$ | H |
| Compound 5 | O—$CH(CH_2CH_3)_2$ | H | O—$CH(CH_2CH_3)_2$ | H |
| Compound 6 | O-cyclopentyl | H | O-cyclopentyl | H |
| Compound 7 | O—Bn | H | O—Bn | H |
| Compound 8 | Cl | H | Cl | H |
| Compound 9 | $SCH_2CH_3$ | H | $SCH_2CH_3$ | H |
| Compound 10 | $CH_3$ | H | CH3 | H |
| Compound 11 | i-Pr | H | i-Pr | H |
| Compound 12 | C(=O)O $CH_3$ | H | C(=O)O $CH_3$ | H |
| Compound 13 | CN | H | CN | H |
| Compound 14 | $CF_3$ | H | $CF_3$ | H |
| Compound 15 | $NO_2$ | H | $NO_2$ | H |
| Compound 16 | $OCF_3$ | H | $OCF_3$ | H |

Embodiment 1: Preparation of Substituted Benzylideneguanidine Derivatives

The substituted benzylideneguanidine derivatives have a structure according to formula (I):

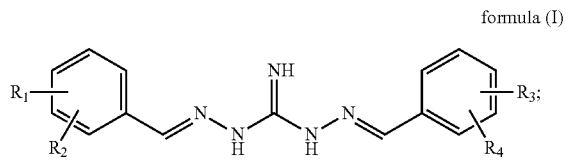

formula (I)

wherein, $R_1$, $R_2$, $R_3$ and $R_4$ are H, CN, $NO_2$, $S(=O)_2CH_3$, C(=O)O—$C_{1-8}$ linear or branched alkyl, halogen, $C_{1-8}$ linear or branched alkyl, $C_{1-8}$ linear or branched alkyl halide, O—$C_{1-14}$ linear or branched alkyl, O—$C_{3-8}$ cycloalkyl, O—$CH_2$-Ph, O-Ph, S—$C_{1-14}$ linear or branched alkyl, or S—$C_{1-14}$ linear or branched alkyl halide;

the halogen is F, Cl, Br or I;

the alkyl halide is an F, Cl, Br, or I substituted alkyl;

the O—$CH_2$-Ph and O-Ph are having a unsubstituted phenyl or a phenyl substituted with one, two, three, or four substituents, the substituents being selected from F, Cl, Br, I, $C_{3-8}$ cycloalkyl, and $C_{1-8}$ linear or branched alkyl.

The substituted benzylideneguanidine derivatives according to formula (I) can be prepared by reacting a substituted benzaldehyde (formula (V) or formula (VI)) with a diaminoguanidine hydrochloride (formula (VII)) to obtain an imine compound according to formula (I).

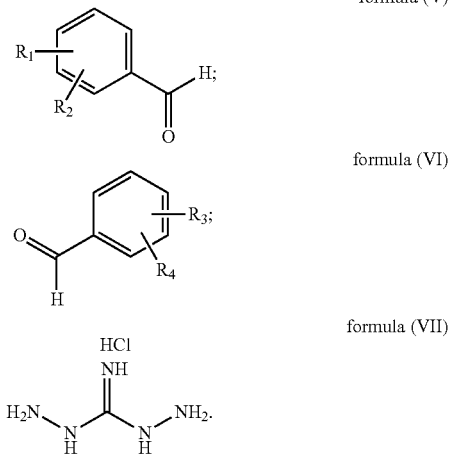

formula (V)

formula (VI)

formula (VII)

The imine compound is a Schiff base, wherein: $R_1$, $R_2$, $R_3$ and $R_4$ are H, CN, $NO_2$, $S(=O)_2CH_3$, $C(=O)O-C_{1-8}$ linear or branched alkyl, halogen, $C_{1-8}$ linear or branched alkyl, $C_{1-8}$ linear or branched alkyl halide, $O-C_{1-14}$ linear or branched alkyl, $O-C_{3-8}$ cycloalkyl, $O-CH_2$-Ph, O-Ph, $S-C_{1-14}$ linear or branched alkyl, or $S-C_{1-14}$ linear or branched alkyl halide; the halogen is F, Cl, Br or I; in the $C_{1-8}$ linear or branched alkyl halide and the $S-C_{1-14}$ linear or branched alkyl halide, the alkyl halide is an F, Cl, Br, or I substituted alkyl; the $O-CH_2$-Ph and O-Ph are having a unsubstituted phenyl or a phenyl substituted with one, two, three, or four substituents, the substituents being selected from F, Cl, Br, I, $C_{3-8}$ cycloalkyl, and $C_{1-8}$ linear or branched alkyl. In this type of reaction, if the groups to which the primary amino group and the aldehyde group are bonded are aliphatic hydrocarbon groups, then the corresponding imine obtained is unstable; however, if one group is an aryl, then the imine will have a stable crystal form, making the reaction shift towards products (*Organic Chemistry, Third Edition*, HU Honh-Wen, page 296). U.S. Pat. Nos. 3,769,432, 3,901,944, 3,941,825, 3,992,446, 4,575,560, WO0040549, WO2014176636, CN1093081A and CN103880712A disclose the imine compounds and provide the corresponding synthetic methods; for imine compounds not mentioned in the above patents, a person skilled in the art can readily prepare hydrochlorides thereof based on the principle provided by *Organic Chemistry* (*Third Edition*, HU Honh-Wen, page 296) in combination with prior art. Other salts of the substituted benzylideneguanidine derivatives of the present invention can be prepared by reacting an imine hydrochloride prepared by the above method with a base such as potassium carbonate or sodium hydroxide to obtain a free alkali, which is then reacted with a corresponding acid in a stoichiometric ratio to form the corresponding substituted benzylideneguanidine derivative salt.

Preparation of Hydrochloride of Compound 3:

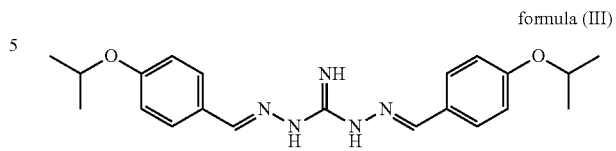

formula (III)

4-isopropoxybenzaldehyde (25 g, 0.153 mol, 2 eq) was dissolved in about 300 ml of ethanol, followed by the addition of diaminoguanidine monohydrochloride (9.56 g, 0.0765 mol, 1 eq). The mixture was stirred at room temperature to allow reaction. The diaminoguanidine monohydrochloride dissolved gradually. The reaction was monitored by TCL until the 4-isopropoxybenzaldehyde was reacted completely. The reaction solution was concentrated to obtain a white solid. The solid was then washed with 400 ml of ethyl acetate under stirring and then subjected to filtration. The filter cake was washed with ethyl acetate for two to three times and then vacuum-dried to obtain a white solid product, which was the hydrochloride of compound 3.

$^1$H (500 MHz, DMSO-$d_6$) δ (ppm): 11.77 (2H, s), 8.29 (4H, s), 7.85 (4H, d), 7.01 (4H, d), 4.72 (2H, m), 1.29 (12H, d).

Preparation of Hydrochloride of Compound 8:

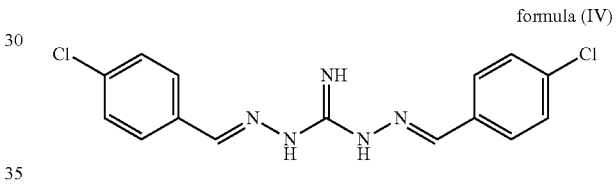

formula (IV)

4-chlorobenzaldehyde (40 g, 0.286 mol, 2 eq) was dissolved in about 300 ml of ethanol, followed by the addition of diaminoguanidine monohydrochloride (17.86 g, 0143 mol, 1 eq). The mixture was stirred at room temperature to allow reaction. The diaminoguanidine monohydrochloride dissolved gradually, followed by the precipitation of a large amount of white solid. The reaction was monitored by TCL until the 4-chlorobenzaldehyde was reacted completely. The reaction solution was subjected to filtration. The filter cake was washed with ethyl acetate for two to three times and then vacuum-dried to obtain a white solid product, which was the hydrochloride of compound 8. $^1$H (500 MHz, DMSO-$d_6$) δ (ppm): 12.52 (2H, s), 8.62 (2H, s), 8.45 (2H, s), 7.988 (4H, d), 7.546 (4H, d).

Embodiment 2: Effect of Substituted Benzylideneguanidine Derivatives in Enhancing the Inhibitory Activity on Colistin Sulfate-Susceptible *Escherichia coli* Strains The substituted benzylideneguanidine derivatives in this embodiment were in the form of a hydrochloride, i.e., the experiments were carried out with hydrochlorides of the substituted benzylideneguanidine derivatives.

Through the doubling dilution method, in vitro minimum inhibitory concentrations (MICs) of colistin sulfate and substituted benzylideneguanidine derivatives against *Escherichia coli* strains (which were susceptible to colistin sulfate, with an MIC value of lower than 4.0 ppm) were measured. In vitro minimum inhibitory concentrations of colistin sulfate against the strains where the cultures respectively comprised 20.0 ppm of the substituted benzylideneguanidine derivatives were also measured (the substituted benzylideneguanidine derivatives and colistin sulfate were combined, wherein the substituted benzylideneguanidine derivatives were employed in a fixed concentration of 20.0 ppm while colistin sulfate was subjected to a serial dilution, in order to measure the in vitro minimum inhibitory concentrations of colistin sulfate against the strains when 20.0 ppm of the substituted benzylideneguanidine derivatives were employed). Results were as shown in Table 2. As can be seen from Table 2, all tested strains were susceptible to colistin sulfate, while all the substituted benzylideneguanidine derivatives did not exhibit inhibitory activity on the tested strains; meanwhile, for the test groups where 20.0 ppm of the substituted benzylideneguanidine derivatives were employed, the minimum inhibitory concentrations of colistin sulfate against the strains had decreased to various extents, about ½ to ¼ of the original levels (see Table 3).

TABLE 2

In vitro minimum inhibitory concentrations (MICs, ppm) of substituted benzylideneguanidine derivatives against colistin sulfate-susceptible *E. coli* strains

|  | E. coli 3Y-9 | E. coli 2S-19 | E. coli 5W-7 | E. coli 3B-24 |
|---|---|---|---|---|
| Colistin sulfate | 2.0 | 2.0 | 1.0 | 2.0 |
| Compound 1 | >800 | >800 | >800 | >800 |
| Compound 2 | >800 | >800 | >800 | >800 |
| Compound 3 | >800 | >800 | >800 | >800 |
| Compound 4 | >800 | >800 | >800 | >800 |
| Compound 5 | >800 | >800 | >800 | >800 |
| Compound 6 | >800 | >800 | >800 | >800 |
| Compound 7 | >800 | >800 | >800 | >800 |
| Compound 8 | >800 | >800 | >800 | >800 |
| Compound 9 | >800 | >800 | >800 | >800 |
| Compound 10 | >800 | >800 | >800 | >800 |
| Compound 11 | >800 | >800 | >800 | >800 |
| Compound 12 | >800 | >800 | >800 | >800 |
| Compound 13 | >800 | >800 | >800 | >800 |
| Compound 14 | >800 | >800 | >800 | >800 |
| Compound 15 | >800 | >800 | >800 | >800 |
| Compound 16 | >800 | >800 | >800 | >800 |

TABLE 3

In vitro minimum inhibitory concentrations (MICs, ppm) of colistin sulfate against colistin sulfate-susceptible *E. coli* strains in the presence of substituted benzylideneguanidine derivatives

|  | E. coli 3Y-9 | E. coli 2S-19 | E. coli 5W-7 | E. coli 3B-24 |
|---|---|---|---|---|
| Colistin sulfate | 2.00 | 2.00 | 1.00 | 2.00 |
| Compound 1 | 1.00 | 1.00 | 0.50 | 1.00 |
| Compound 2 | 2.00 | 2.00 | 1.00 | 2.00 |
| Compound 3 | 0.50 | 0.50 | 0.25 | 0.50 |
| Compound 4 | 1.00 | 1.00 | 0.50 | 1.00 |
| Compound 5 | 2.00 | 1.00 | 1.00 | 2.00 |
| Compound 6 | 1.00 | 1.00 | 0.50 | 1.00 |
| Compound 7 | 2.00 | 2.00 | 1.00 | 2.00 |
| Compound 8 | 1.00 | 1.00 | 0.50 | 1.00 |
| Compound 9 | 1.00 | 1.00 | 0.50 | 1.00 |
| Compound 10 | 1.00 | 1.00 | 0.50 | 1.00 |
| Compound 11 | 1.00 | 1.00 | 0.50 | 2.00 |
| Compound 12 | 1.00 | 1.00 | 0.50 | 1.00 |
| Compound 13 | 1.00 | 1.00 | 0.50 | 0.50 |
| Compound 14 | 1.00 | 1.00 | 0.50 | 1.00 |
| Compound 15 | 1.00 | 1.00 | 0.50 | 1.00 |
| Compound 16 | 2.00 | 1.00 | 0.50 | 1.00 |

Note:
The colistin sulfate group was a control group without benzylideneguanidine derivatives.

Embodiment 3: Effect of Substituted Benzylideneguanidine Derivatives in Enhancing the Inhibitory Activity on Colistin Sulfate-Resistant *Escherichia coli* Strains The substituted benzylideneguanidine derivatives in this embodiment were in the form of a hydrochloride, i.e., the experiments were carried out with hydrochlorides of the substituted benzylideneguanidine derivatives.

Through the doubling dilution method, in vitro minimum inhibitory concentrations (MICs) of colistin sulfate and substituted benzylideneguanidine derivatives against colistin sulfate-resistant *E. coli* strains (which were resistant to colistin sulfate, with an MIC value of higher than 4.0 ppm) were measured. In vitro minimum inhibitory concentrations of colistin sulfate against the strains where the cultures respectively comprised 20.0 ppm of the substituted benzylideneguanidine derivatives were also measured. Results showed that, all tested strains were resistant to colistin sulfate, and all the substituted benzylideneguanidine derivatives did not exhibit inhibitory activity on the tested strains (see Table 4); meanwhile, for the test groups where 20.0 ppm of the substituted benzylideneguanidine derivatives were employed, the minimum inhibitory concentrations of colistin sulfate against the strains had decreased to various extents, about ¹⁄₅₀ to ¹⁄₁₀₀ of the original levels (see Table 5).

TABLE 4

In vitro minimum inhibitory concentrations (MICs, ppm) of substituted benzylideneguanidine derivatives against colistin sulfate-resistant *E. coli* strains

|  | E. coli 2G-7 | E. coli 5F-1 | E. coli 4D-6 | E. coli 3H-4 |
|---|---|---|---|---|
| Colistin sulfate | 64 | 128 | 256 | 64 |
| Compound 1 | >800 | >800 | >800 | >800 |
| Compound 2 | >800 | >800 | >800 | >800 |
| Compound 3 | >800 | >800 | >800 | >800 |
| Compound 4 | >800 | >800 | >800 | >800 |
| Compound 5 | >800 | >800 | >800 | >800 |
| Compound 6 | >800 | >800 | >800 | >800 |
| Compound 7 | >800 | >800 | >800 | >800 |
| Compound 8 | >800 | >800 | >800 | >800 |
| Compound 9 | >800 | >800 | >800 | >800 |
| Compound 10 | >800 | >800 | >800 | >800 |
| Compound 11 | >800 | >800 | >800 | >800 |
| Compound 12 | >800 | >800 | >800 | >800 |
| Compound 13 | >800 | >800 | >800 | >800 |
| Compound 14 | >800 | >800 | >800 | >800 |
| Compound 15 | >800 | >800 | >800 | >800 |
| Compound 16 | >800 | >800 | >800 | >800 |

TABLE 5

In vitro minimum inhibitory concentrations (MICs, ppm) of colistin sulfate against colistin sulfate-resistant *E. coli* strains in the presence of substituted benzylideneguanidine derivatives

|  | E. coli 2G-7 | E. coli 5F-1 | E. coli 4D-6 | E. coli 3H-4 |
|---|---|---|---|---|
| Colistin sulfate | 64.0 | 128.0 | 256.0 | 64.0 |
| Compound 1 | 1.0 | 2.0 | 4.0 | 2.0 |
| Compound 2 | 2.0 | 4.0 | 8.0 | 2.0 |
| Compound 3 | 1.0 | 1.0 | 2.0 | 0.5 |
| Compound 4 | 4.0 | 8.0 | 16 | 4 |
| Compound 5 | 8 | 16 | 32 | 8 |
| Compound 6 | 4 | 8 | 16 | 4 |
| Compound 7 | 8 | 8 | 32 | 8 |
| Compound 8 | 4 | 8 | 16 | 4 |
| Compound 9 | 4 | 8 | 16 | 4 |

TABLE 5-continued

In vitro minimum inhibitory concentrations (MICs, ppm) of colistin
sulfate against colistin sulfate-resistant *E. coli* strains in
the presence of substituted benzylideneguanidine derivatives

|  | *E. coli* 2G-7 | *E. coli* 5F-1 | *E. coli* 4D-6 | *E. coli* 3H-4 |
|---|---|---|---|---|
| Compound 10 | 4 | 8 | 16 | 4 |
| Compound 11 | 16 | 16 | 64 | 16 |
| Compound 12 | 4 | 8 | 16 | 4 |
| Compound 13 | 4 | 8 | 16 | 4 |
| Compound 14 | 16 | 32 | 32 | 8 |
| Compound 15 | 4 | 8 | 16 | 4 |
| Compound 16 | 8 | 16 | 32 | 8 |

Note:
The colistin sulfate group was a control blank; for the other groups, the cultures comprised 20.0 ppm of different substituted benzylideneguanidine derivatives.

Embodiment 4: Resistance Reversing Effect of Compound 3 in Various Concentrations on Various Colistin Sulfate-Resistant Species The compound 3 in this embodiment was in the form of a hydrochloride, i.e., the experiments were carried out with a hydrochloride of compound 3.

Through the doubling dilution method, in vitro minimum inhibitory concentrations (MICs) of colistin sulfate and compound 3 against various colistin sulfate-resistant Gram-negative bacteria (which were resistant to colistin sulfate, with an MIC value of higher than 4.0 ppm) were measured. In vitro minimum inhibitory concentrations of colistin sulfate against the strains where the cultures respectively comprised various concentrations of compound 3 were also measured. Results showed that, all tested strains were resistant to colistin sulfate, and compound 3 did not exhibit inhibitory activity on all the tested strains; meanwhile, for the test groups where compound 3 was employed, the minimum inhibitory concentrations of colistin sulfate against the strains had decreased to various extents, in an obvious dosage-dependent way (see Table 6).

TABLE 6

In vitro minimum inhibitory concentrations (MICs, ppm) of colistin sulfate against
various species in the presence of various concentrations of compound 3

| Compound 3 (ppm) | *E. coli* 5F-1 | *P. aeruginosa* E543 | *Salmonella* sp. 3087 | *Shigella* sp. 2D89 | *Klebsiella* sp. 4125 |
|---|---|---|---|---|---|
| 0 | 128.00 | 64.00 | 128.00 | 32.00 | 64.00 |
| 5 | 32.00 | 32.00 | 64.00 | 16.00 | 32.00 |
| 10 | 8.00 | 8.00 | 16.00 | 2.00 | 8.00 |
| 20 | 1.00 | 2.00 | 4.00 | 1.00 | 2.00 |
| 40 | 1.00 | 0.50 | 2.00 | 0.25 | 1.00 |
| 80 | 0.50 | 0.50 | 1.00 | 0.25 | 1.00 |
| Compound 3 | >800 | >800 | >800 | >800 | >800 |

Note:
For the compound 3 group, in vitro minimum inhibitory concentrations of compound 3 against various species were measured in the absence of colistin sulfate.

Embodiment 5: Synergy of Substituted Benzylideneguanidine Derivatives and Colistin Sulfate in the Feed for Weanling Piglets The substituted benzylideneguanidine derivatives in this embodiment were in the form of a hydrochloride, i.e., the experiments were carried out with hydrochlorides of the substituted benzylideneguanidine derivatives.

90 28-day-aged Duroc×Landrace×Large crossbred lean weanling piglets similar in weight were divided into 9 groups, 10 piglets in each group. For each group, colistin sulfate and/or various substituted benzylideneguanidine derivatives were added into the antibiotic-free creep feed. The piglets were given ad libitum access to feed and water during the experiment. Weight gain, feed efficiency and diarrhea rate of each group within ten days were recorded. Results showed that (see Table 7), the addition of colistin sulfate into the feed for weanling piglets failed to effectively reduce the diarrhea rate, and obvious improvement in weight gain or feed efficiency was not observed; on the other hand, for the groups in which colistin sulfate was added along with the substituted benzylideneguanidine derivatives, the diarrhea rate was reduced to various extents and the productivity was improved to various extents.

TABLE 7

Synergy of substituted benzylideneguanidine derivatives
and colistin sulfate in the feed for weanling piglets

| Group | Quantity | Antibacterial | Dosage (ppm) | Diarrhea rate (%) | Average daily weight gain (g) | Feed conversion ratio |
|---|---|---|---|---|---|---|
| 1 | 10 | Blank | 0 | 36 | 216 | 1.663 |
| 2 | 10 | Control | 20 | 33 | 219 | 1.649 |
| 3 | 10 | Compound 1 | 150 | 18 | 243 | 1.529 |
| 4 | 10 | Compound 3 | 150 | 8 | 258 | 1.441 |
| 5 | 10 | Compound 4 | 150 | 19 | 239 | 1.532 |
| 6 | 10 | Compound 5 | 150 | 25 | 231 | 1.565 |
| 7 | 10 | Compound 6 | 150 | 31 | 226 | 1.642 |
| 8 | 10 | Compound 7 | 150 | 16 | 240 | 1.576 |
| 9 | 10 | Compound 8 | 150 | 33 | 220 | 1.608 |

Note:
For the blank group, no colistin sulfate or substituted benzylideneguanidine derivative was added to the creep feed. For the control group, only 20 ppm of colistin sulfate was added to the creep feed. For the other groups, 20 ppm of colistin sulfate and 150 ppm of substituted benzylideneguanidine derivatives were added to the creep feed.

Embodiment 6: Synergy of Compound 3 and Colistin Sulfate in the Feed for Weanling Piglets The compound 3 in this embodiment was in the form of a hydrochloride, i.e., the experiments were carried out with a hydrochloride of compound 3.

120 28-day-aged Duroc×Landrace×Large crossbred lean weanling piglets similar in weight were divided into 12 groups, 10 piglets in each group. For each group, colistin sulfate and/or compound 3 were added into the antibiotic-free creep feed. The piglets were given ad libitum access to feed and water during the experiment. Weight gain, feed efficiency and diarrhea rate of each group within ten days were recorded. Results showed that, the addition of colistin sulfate or compound 3 into the feed for weanling piglets failed to effectively reduce the diarrhea rate, and obvious improvement in weight gain or feed efficiency was not observed; on the other hand, for the groups in which colistin sulfate was added together with compound 3 (groups 10, 11 and 12), the diarrhea rate was reduced by 20%, and the weight gain and feed efficiency were improved significantly (see Table 8).

TABLE 8

Effect of compound 3 and colistin sulfate in the feed for weanling piglets

| Group | Quantity | Antibacterial | Dosage (ppm) | Diarrhea rate (%) | Average daily weight gain (g) | Feed conversion ratio |
|---|---|---|---|---|---|---|
| 1 | 10 | Blank | 0 | 35 | 204 | 1.648 |
| 2 | 10 | Blank | 0 | 37 | 201 | 1.672 |
| 3 | 10 | Blank | 0 | 34 | 196 | 1.656 |
| 4 | 10 | Control 1 | 20 | 31 | 215 | 1.654 |
| 5 | 10 | Control 1 | 20 | 29 | 208 | 1.598 |
| 6 | 10 | Control 1 | 20 | 33 | 217 | 1.623 |
| 7 | 10 | Control 2 | 150 | 36 | 200 | 1.666 |
| 8 | 10 | Control 2 | 150 | 38 | 205 | 1.639 |
| 9 | 10 | Control 2 | 150 | 34 | 211 | 1.647 |
| 10 | 10 | Test | 20 + 150 | 12 | 254 | 1.435 |
| 11 | 10 | Test | 20 + 150 | 9 | 248 | 1.427 |
| 12 | 10 | Test | 20 + 150 | 10 | 251 | 1.453 |

Note:
For the blank group, no colistin sulfate or substituted benzylideneguanidine derivative was added to the creep feed. For the control group, only 20 ppm of colistin sulfate was added to the creep feed. For the test groups, 20 ppm of colistin sulfate and 150 ppm of compound 3 were added to the creep feed.

Embodiment 7: Synergy of Compound 3 in Various Dosages and Colistin Sulfate in the Feed for Weanling Piglets The compound 3 in this embodiment was in the form of a hydrochloride, i.e., the experiments were carried out with a hydrochloride of compound 3.

90 28-day-aged Duroc×Landrace×Large crossbred lean weanling piglets similar in weight were divided into 9 groups, 10 piglets in each group. For each group, colistin sulfate and/or various dosages of compound 3 were added into the antibiotic-free creep feed. The piglets were given ad libitum access to feed and water during the experiment. Weight gain, feed efficiency and diarrhea rate of each group within ten days were recorded. Results showed that, the addition of colistin sulfate or compound 3 into the feed for weanling piglets provided limited improvements in the diarrhea rate, weight gain, and feed efficiency; on the other hand, for the groups in which colistin sulfate was added together with compound 3, improvements in the diarrhea rate and productivity were observed, in a dosage-dependent way that a higher dosage of compound 3 led to a better effect (see Table 9).

TABLE 9

Effect of various dosages of compound 3 and colistin sulfate in the feed for weanling piglets

| Group | Quantity | Antibacterial | Dosage (ppm) | Diarrhea rate (%) | Average daily weight gain (g) | Feed conversion ratio |
|---|---|---|---|---|---|---|
| 1 | 10 | Blank | 0 | 34 | 208 | 1.684 |
| 2 | 10 | Control | 0 | 33 | 211 | 1.672 |
| 3 | 10 | Test 1 | 10 | 30 | 215 | 1.632 |
| 4 | 10 | Test 2 | 25 | 26 | 226 | 1.578 |
| 5 | 10 | Test 3 | 50 | 20 | 237 | 1.532 |
| 6 | 10 | Test 4 | 100 | 16 | 248 | 1.499 |
| 7 | 10 | Test 5 | 200 | 6 | 255 | 1.417 |
| 8 | 10 | Test 6 | 500 | 3 | 259 | 1.428 |
| 9 | 10 | Compound 3 | 200 | 29 | 228 | 1.596 |

Note:
For the blank group, no colistin sulfate or substituted benzylideneguanidine derivative was added to the creep feed. For the control group, only 20 ppm of colistin sulfate was added to the creep feed. For the test groups, 20 ppm of colistin sulfate and various dosages of compound 3 were added to the creep feed. For the compound 3 group, only 200 ppm of compound 3 was added to the creep feed.

Embodiment 8: Effect of Combined Application of Compound 3 and Colistin Sulfate in Chicken Feed The compound 3 in this embodiment was in the form of a hydrochloride, i.e., the experiments were carried out with a hydrochloride of compound 3.

800 1-day-aged fast-growing yellow feather broilers were divided into 4 groups, 4 parallels in each group and 50 broilers in each parallel. For each group, colistin sulfate and/or compound 3 were added into the feed. The chicken were kept in cages and given ad libitum access to feed and water during a 28-day experiment. Synergy of compound 3 and colistin sulfate on the chicken in the weight gain and feed efficiency was observed from the result (see Table 10).

TABLE 10

Effect of combined application of compound 3 and colistin sulfate in chicken feed

| Group | Quantity | Drug | Dosage (ppm) | Survival rate (%) | Average daily weight gain (g) | Feed conversion ratio |
|---|---|---|---|---|---|---|
| 1 | 50 × 4 | Blank | 0 | 100% | 37.6 | 2.088 |
| 2 | 50 × 4 | Colistin sulfate | 50 | 100% | 39.8 | 1.965 |
| 3 | 50 × 4 | Compound 3 | 100 | 100% | 40.2 | 1.943 |
| 4 | 50 × 4 | Test | 20 + 50 | 100% | 44.6 | 1.855 |

Note:
For the blank group, no colistin sulfate or compound3 was added to the feed. For the colistin sulfate group, 50 ppm of colistin sulfate was added to the feed. For the compound 3 group, 100 ppm of compound 3 was added to the feed. For the test group, 20 ppm of colistin sulfate and 50 ppm of compound 3 were added to the feed.

Embodiment 9: Effect of Combined Application of Compound 3 and Colistin Sulfate in Duck Feed The compound 3 in this embodiment was in the form of a hydrochloride, i.e., the experiments were carried out with a hydrochloride of compound 3.

800 1-day-aged cherry valley ducks were divided into 4 groups according to Table 10, 4 parallels in each group and 50 ducks in each parallel. For each group, colistin sulfate and/or compound 3 were added into the feed. The ducks were kept in cages and given ad libitum access to feed and water during a 21-day experiment. Synergy of compound 3 and colistin sulfate on the ducks in the weight gain and feed efficiency was observed from the result (see Table 11).

TABLE 11

Effect of combined application of compound 3 and colistin sulfate in duck feed

| Group | Quantity | Drug | Dosage (ppm) | Survival rate (%) | Average daily weight gain (g) | Feed conversion ratio |
|---|---|---|---|---|---|---|
| 1 | 50 × 4 | Blank | 0 | 100% | 48.2 | 2.087 |
| 2 | 50 × 4 | Colistin sulfate | 40 | 100% | 50.1 | 1.945 |
| 3 | 50 × 4 | Compound 3 | 100 | 100% | 50.5 | 1.926 |
| 4 | 50 × 4 | Test | 20 + 50 | 100% | 55.6 | 1.817 |

Note:
For the blank group, no colistin sulfate or compound3 was added to the feed. For the colistin sulfate group, 40 ppm of colistin sulfate was added to the feed. For the compound 3 group, 100 ppm of compound 3 was added to the feed. For the test group, 20 ppm of colistin sulfate and 50 ppm of compound 3 were added to the feed.

What is claimed is:

1. A method of using a substituted benzylideneguanidine derivative, a stereoisomer thereof, a geometric isomer thereof, a tautomer thereof, a hydrate thereof, a solvate thereof, a metabolite thereof, a pharmaceutically acceptable salt thereof, a prodrug thereof, or a composite comprising the substituted benzylideneguanidine derivative, as a synergist for a polymyxin antibiotic, comprising:
   (a) adding to a feed a combination of (1) the polymyxin antibiotic and (2) the substituted benzylideneguanidine derivative, the stereoisomer thereof, the geometric isomer thereof, the tautomer thereof, the hydrate thereof, the solvate thereof, the metabolite thereof, the pharmaceutically acceptable salt thereof, the prodrug thereof, or the composite comprising the substituted benzylideneguanidine derivative, and
   (b) feeding an animal, the feed;
   wherein the substituted benzylideneguanidine derivative has a structure according to formula (I)

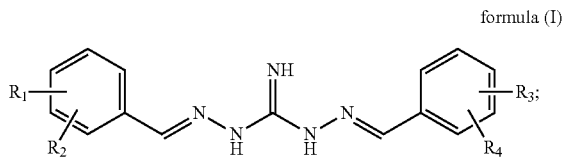

wherein, $R_1$ and $R_3$ are both $O-C_{1-14}$ linear or branched alkyl, and $R_2$ and $R_4$ are both H.

2. The method according to claim 1, wherein, the substituted benzylideneguanidine derivative has a structure according to formula (III):

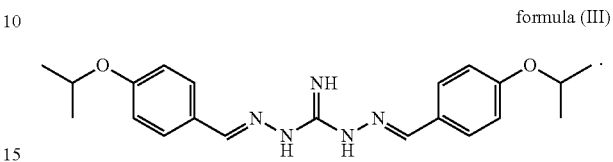

formula (III)

3. The method according to claim 1, wherein, the pharmaceutically acceptable salt of the substituted benzylideneguanidine derivative is a hydrochloride, a phosphate, a sulfate, an acetate, a lactate, a methanesulfonate, a 2-hydroxyethylsulfonate, a succinate, a benzoate, a tartrate, a citrate, a lysine salt, a fumarate or a maleate of the substituted benzylideneguanidine derivative.

4. The method according to claim 1, wherein, the polymyxin antibiotic is any one of polymyxin A, polymyxin B, polymyxin C, polymyxin D, polymyxin E, or pharmaceutically acceptable salts or prodrugs of the polymyxin A, polymyxin B, polymyxin C, polymyxin D or polymyxin E.

5. The method according to claim 4, wherein, the polymyxin antibiotic is colistin sulfate or polymyxin E sodium methanesulfonate.

6. The method according to claim 1, wherein, the substituted benzylideneguanidine derivative, the stereoisomer thereof, the geometric isomer thereof, the tautomer thereof, the hydrate thereof, the solvate thereof, the metabolite thereof, the pharmaceutically acceptable salt thereof, the prodrug thereof, or the composite comprising the substituted benzylideneguanidine derivative, is used in combination with the polymyxin antibiotic, in a form of a pharmaceutical composition for the animal.

7. The method according to claim 6, wherein, the pharmaceutical composition is in a form of a premix, oral solution, soluble powder, tablet, granule, or pulvis.

8. The method according to claim 6, wherein, the animal is a pig, chicken, duck, goose, pigeon, rabbit, mouse, canine, cat, cattle, sheep, horse, or donkey.

* * * * *